US00PP08010P

United States Patent [19]

Thome

[11] Patent Number: Plant 8,010

[45] Date of Patent: Oct. 20, 1992

[54] APPLE TREE: TF808

[75] Inventor: Harold Thome, Comstock Park, Mich.

[73] Assignee: Inter-Plant Patent Marketing, Inc., Niagara-On-The-Lake, Canada

[21] Appl. No.: 444,451

[22] Filed: Dec. 1, 1989

[51] Int. Cl.[5] ..... A01H 5/00
[52] U.S. Cl. ..... Plt./34.1
[58] Field of Search ..... Plt./34, 35

[56] References Cited

PUBLICATIONS

Brooks, R. M., et al. "Empire" *Register of New Fruit and Nut Varieties* 2nd Ed., Univ. of California Press, Berkeley 1972, p. 31.

*Primary Examiner*—Howard J. Locker
*Attorney, Agent, or Firm*—Dykema Gossett

[57] ABSTRACT

A whole-tree mutation of "Empire" designated TF808 demonstrates development of red fruit coloration 5–7 days earlier than "Empire" allowing early harvest.

6 Drawing Sheets

BACKGROUND AND SUMMARY OF THE INVENTION

This distinct and new apple cultivar was discovered as a whole tree mutation growing in the orchard of Mr. Harold Thome, 2137 Seven Mile Road, Comstock Park, Mich. 49321 in the fall of 1985. With respect to those characteristics of TF 808 which have been systematically observed, it is similar in most characteristics to the parent "Empire" but differs from it in a greater density of red coloration of the fruit and the earlier maturity by color development (5 to 7 days) of the fruit as compared to the parent as grown in the same geographical area under similar conditions. The deeper red color at maturity and the substantially earlier date of color development of TF808 are consistently observed and have not been observed to occur in the parental "Empire" variety. For example, FIG. 3 clearly depicts the significantly earlier development of red coloration of TF808 fruit (right) in comparison with "Empire" (left) under virtually identical growing conditions. Based on systematic observations of the parental variety and TF808 over a period of many years, it has been established that the significant difference in color density and date of color maturity of TF808 and the parent, "Empire," is not due to phenotypic variability of "Empire" but rather reflects genotypic variation.

Although the ripeness as measured by ethylene content and the sugar content develop at approximately the same rate in TF808 and "Empire", the earlier development of red coloration in TF808 allows an earlier harvest than with "Empire." It has also been observed that the fruit lenticels are somewhat more conspicuous than those of "Empire." This is due to a greater number of lenticels, a slight increase in average lenticel size and the contrast presented by the deeper red color of TF808.

In addition to these distinguishing characteristics, it has been observed that the shape of the mature fruit is somewhat more pointed on average than "Empire" and that the exposed fruit flesh of TF808 is slightly darker than "Empire." The flower petals of TF808 have a slight pink to red cast as opposed to the predominately white petals of "Empire." Based on fruit bearing characteristics, TF808 appears to be self-incompatible for pollination. Asexual propagation of the new cultivar by grafting as performed in Michigan has shown conclusively that all characteristic botanical features of this cultivar are faithfully reproduced from generation to generation and appear to be firmly fixed.

DETAILED DESCRIPTION OF THE INVENTION

Figure 1:
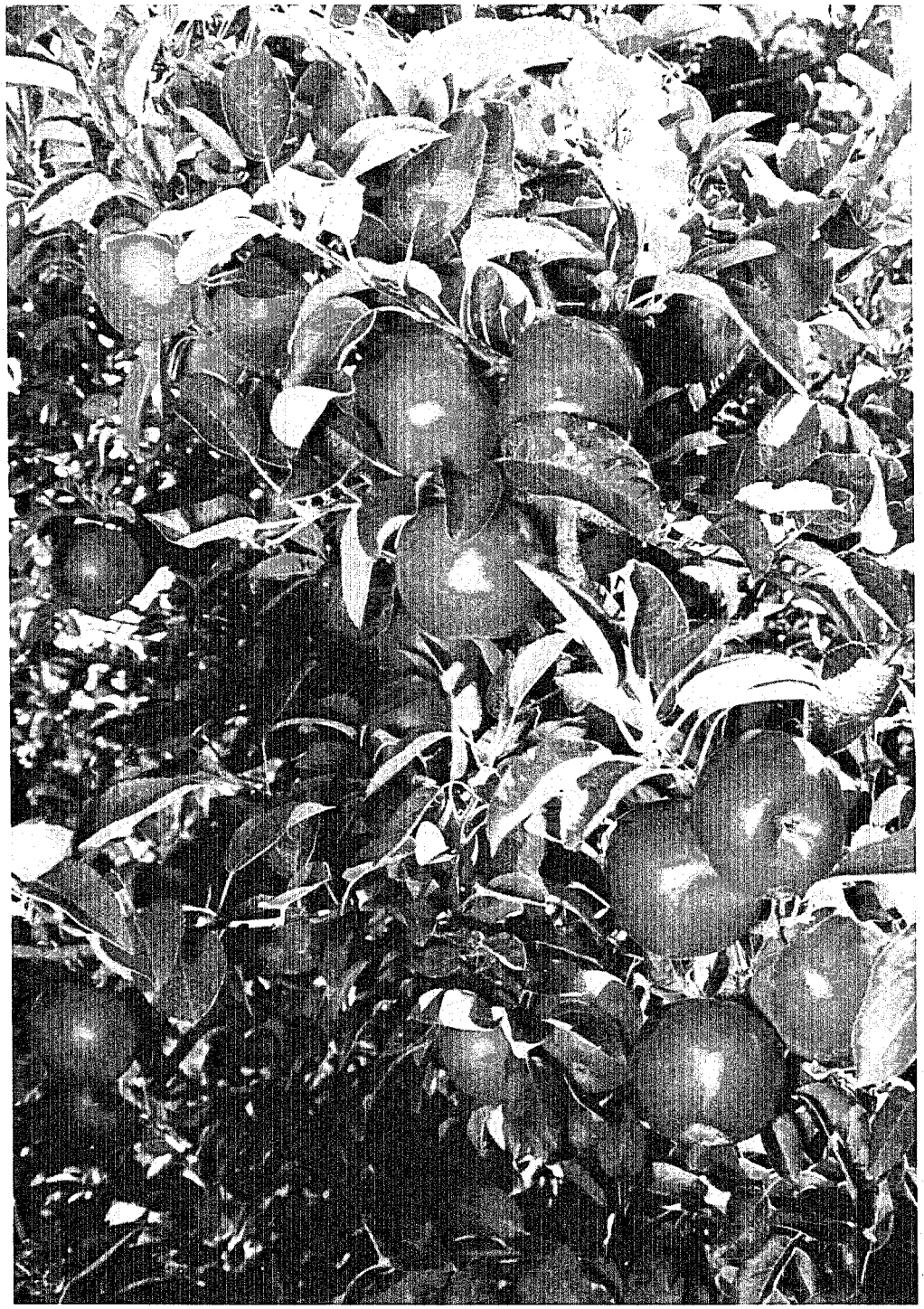
FIG. 1 depicts the fruit, leaves and branches of TF808.
Figure 2:
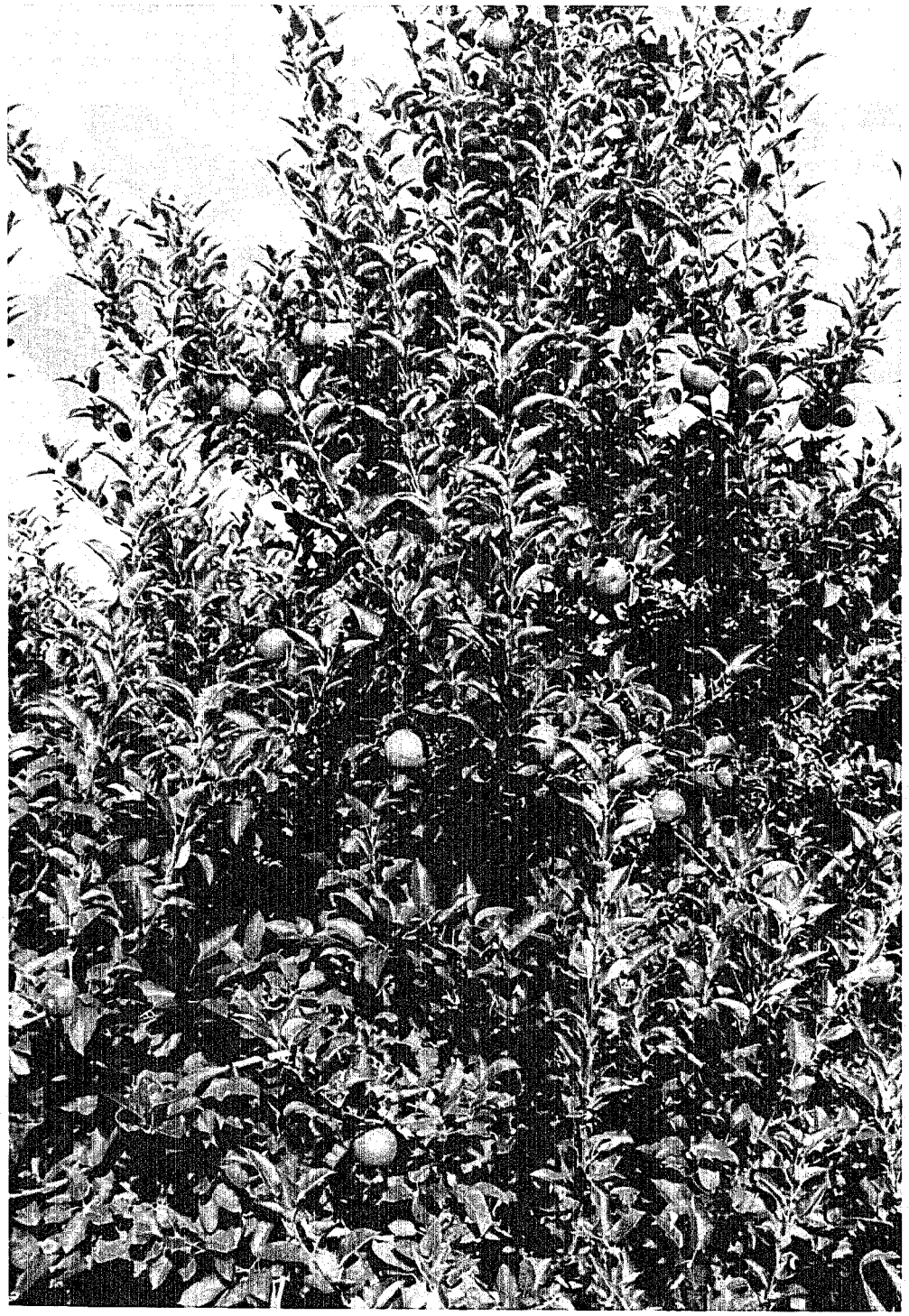
FIG. 2 depicts a typical TF808 tree with fruit.
Figure 3:
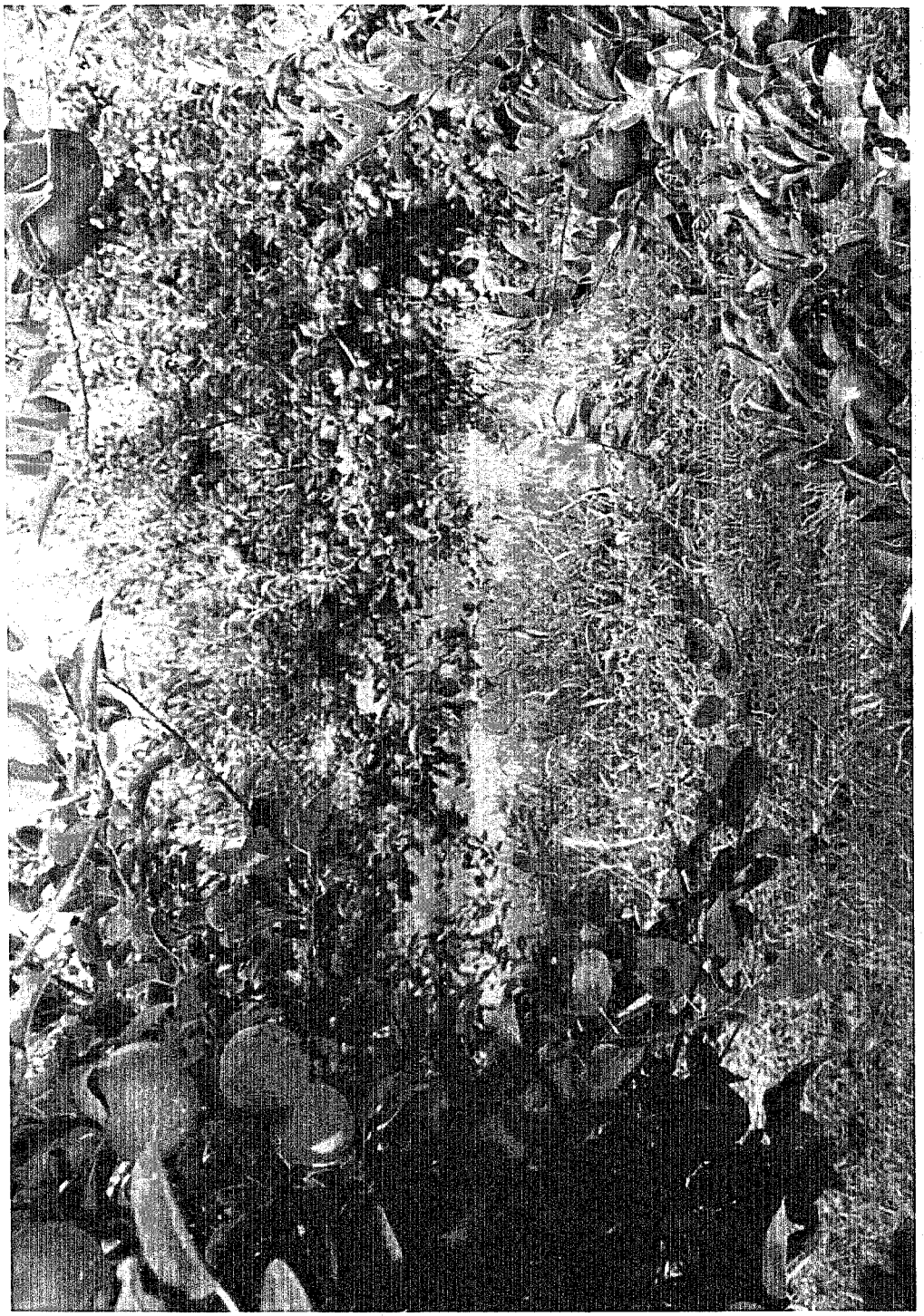
FIG. 3 depicts a comparison of TF808 (right) with the parent "Empire" (left).
Figure 4:
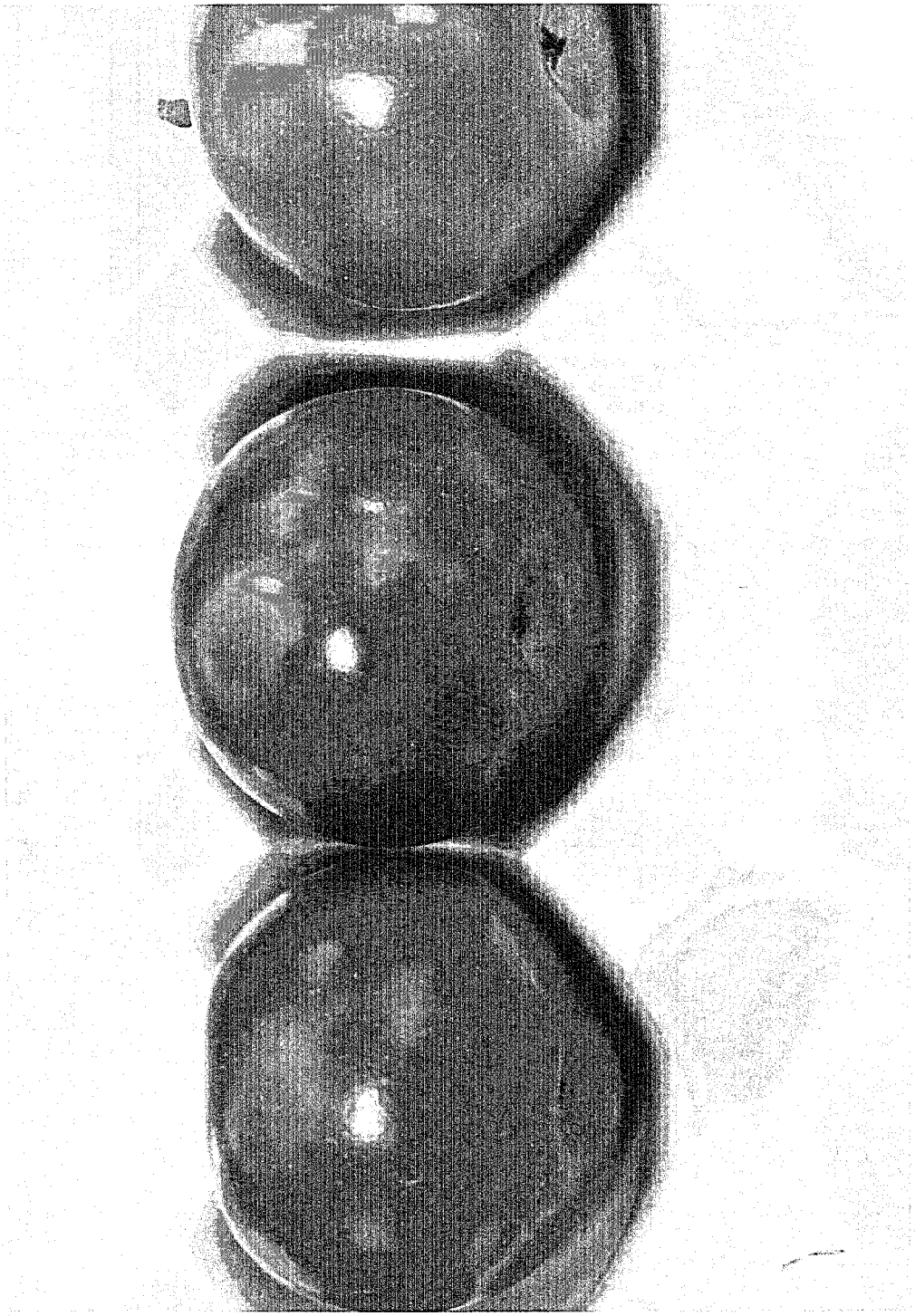
FIG. 4 depicts a side view of mature TF808 fruit.
Figure 5:
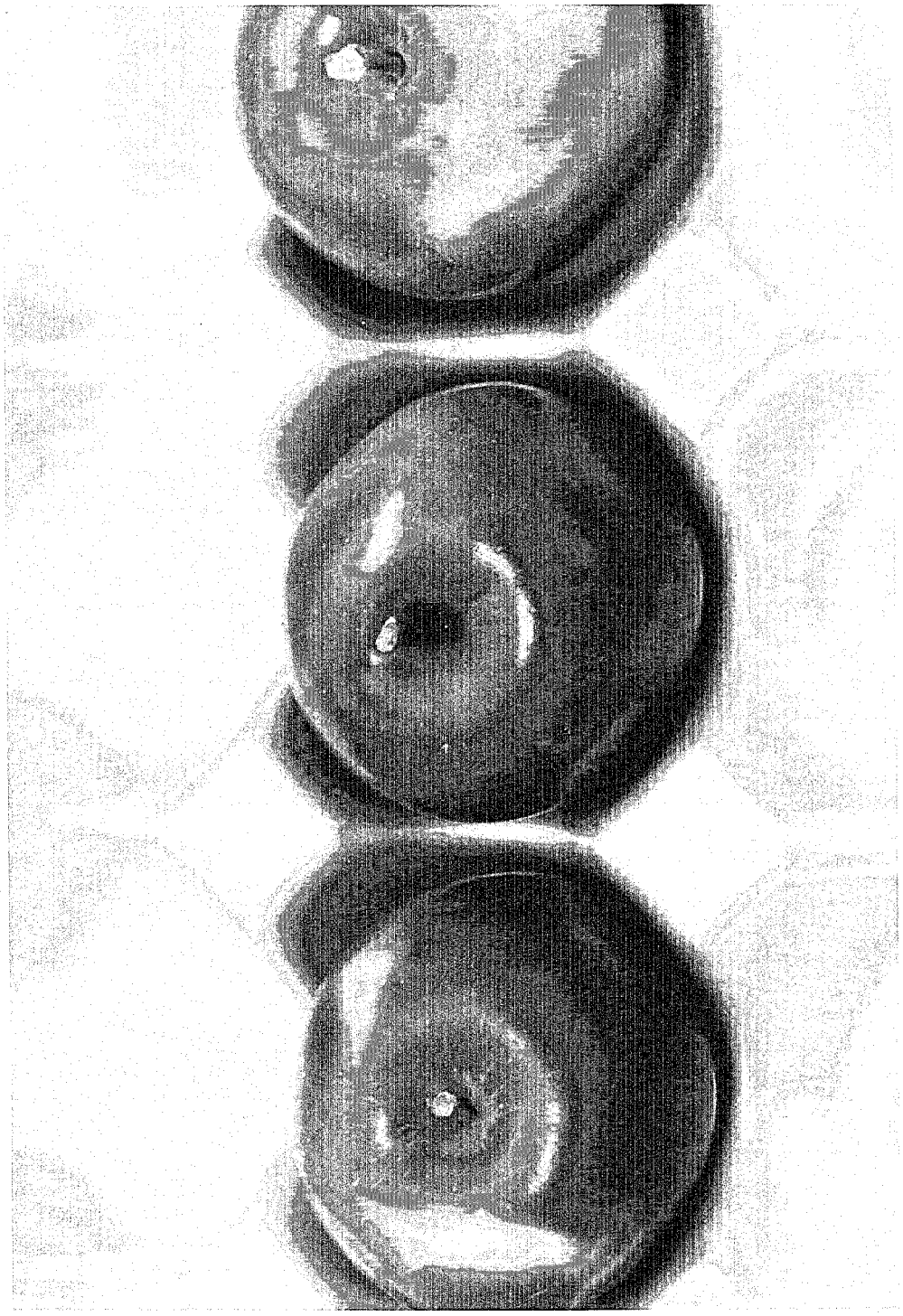
FIG. 5 depicts a top view of mature TF808 fruit.
Figure 6:
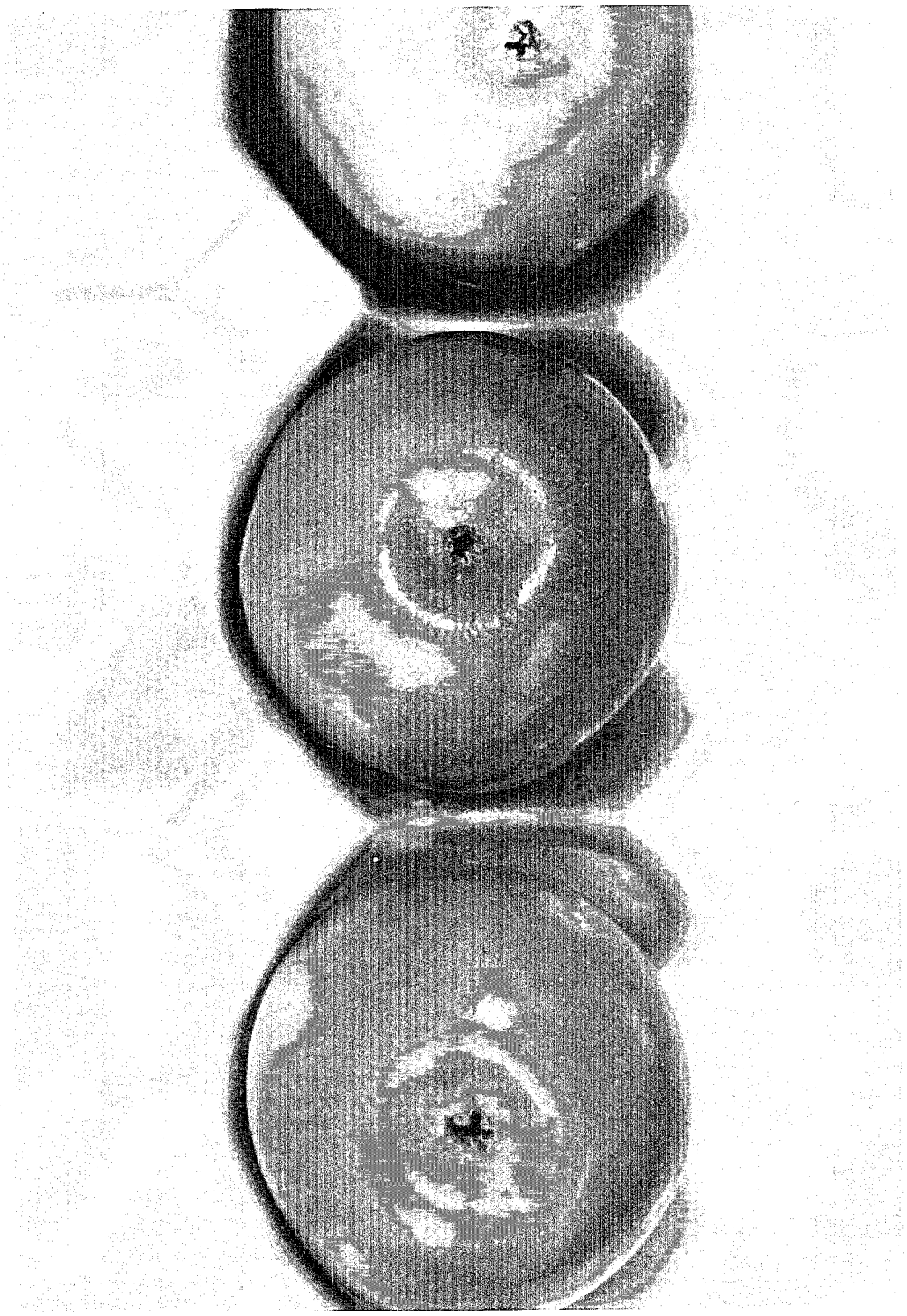
FIG. 6 depicts a bottom view of mature TF808 fruit.

Color designations are according to the Horticultural Colour Chart issued by the British Colour Council in collaboration with The British Royal Horticultural Society.

FLOWER

Pedicel: 1.7 to 2.8 cm in length.
Corolla: 2.2 to 3.1 cm in length.
Date of flowering: Same as parent variety.
Size: Same as parent variety.
Color: Pink to red cast to petals with red stem.
Pollination: Cross-pollination; self-imcompatible based on bearing characteristics.

FRUIT

Shape: Round to slightly oblate, slightly lopsided
Size: Medium, axial diameter 6.2 to 7.0 cm; transverse diameter 6.4 to 7.8 cm.
Color: Indian Lake (Plate 826/1) dark red on blush side of mature fruit as a wash over 70–85% of the fruit surface. No indication of any striping on the background or on the immature fruit. Moderate to heavy "bloom" over entire fruit surface at maturity. Ground color same as "Empire."
Skin: Smooth, waxy with small, scattered round dots.
Stem: 1.8 to 2.2 cm in length, thick and slightly clubbed with 50–60% extending beyond the cavity.

Cavity: Smooth, acute, medium in depth and width, non-russetted, non-pubescent.

Basin: Shallow, broad with sloping sides, smooth surface, slightly lobed along the outer rim.

Calyx: Persistent, open, separate at the base, erect to slightly recurved.

Calyx tube: Deeply conical.

Stamens: Median.

Core line: Meeting.

Core: Distal, closed.

Carpels: Elongated, mucronate, smooth.

Seeds: 0.6 to 0.9 cm in length, accuminate, smooth, dark brown.

Flesh: Fine, white, crisp, firm, mildly sub-acid, slightly aromatic, very good.

Maturity season: 5 to 7 days before "Empire" based on color development.

Uses: Fresh eating, culinary, fresh market.

Keeping quality: Excellent.

Harvest date: Approximately 7 days earlier than parent.

Mature fruit:

*Shape.*—Slightly more pointed than parent.

*Size.*—Same as parent.

*Color of exposed fruit.*—Darker than parent.

*Sugar content.*—Same as parent.

Production of average tree: Consistently more abundant than parent.

TREE

Growth habit: Vigorous, spreading, non-spur type of fruiting habit and in most tree characteristics identical to "Empire".

Leaves: Medium-sized, dark green, simple, ovate base, leaf margins simple serrated upper surface smooth, lower surface dull with slight pubescence. Midrib and primary veins raised with midrib showing characteristic reddish color.

Bark: Same as "Empire".

Leaf size:

*Length.*—5.0 to 10.0 cm.

*Width.*—3.5 to 6.2 cm.

Petiole: 3.0 to 4.5 cm, medium thickness, pubescent, with reddish color developing primarily on the undersurface and extending up into the leaf midrib.

One year shoots: Reddish brown in color, slightly pubescent near the shoot tips, internode length 2.0 to 2.8 cm.

Lenticels: Significantly more pronounced than parent.

What is claimed:

1. A new and distinct apple tree, as shown and described.

* * * * *